US010675319B2

(12) United States Patent
Lin et al.

(10) Patent No.: US 10,675,319 B2
(45) Date of Patent: Jun. 9, 2020

(54) METHOD FOR REGULATING CIRCADIAN CLOCK, REGULATING DIURNAL PREFERENCE, ADJUSTING A BIOLOGICAL CLOCK, IMPROVING SLEEP QUALITY AND/OR FACILITATING SLEEP BY USING MOMORDICA CHARANTIA EXTRACT

(71) Applicant: TCI CO., LTD, Taipei (TW)

(72) Inventors: Yung-Hsiang Lin, Taipei (TW); I-Hui Chen, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 16/169,608

(22) Filed: Oct. 24, 2018

(65) Prior Publication Data

US 2019/0054133 A1 Feb. 21, 2019

Related U.S. Application Data

(63) Continuation-in-part of application No. 15/629,058, filed on Jun. 21, 2017, now abandoned.

(60) Provisional application No. 62/352,767, filed on Jun. 21, 2016.

(51) Int. Cl.
| | |
|---|---|
| *A61K 36/42* | (2006.01) |
| *A61P 3/10* | (2006.01) |
| *A23L 33/105* | (2016.01) |
| *A61P 35/00* | (2006.01) |

(52) U.S. Cl.
CPC .......... *A61K 36/42* (2013.01); *A23L 33/105* (2016.08); *A61P 3/10* (2018.01); *A61P 35/00* (2018.01)

(58) Field of Classification Search
None
See application file for complete search history.

(56) References Cited

U.S. PATENT DOCUMENTS

| | | | | |
|---|---|---|---|---|
| 2006/0040003 | A1* | 2/2006 | Needleman | A61K 31/405 424/757 |
| 2006/0172020 | A1 | 8/2006 | Djang | |
| 2014/0087012 | A1 | 3/2014 | Sharma et al. | |
| 2014/0193391 | A1 | 7/2014 | Pernodet et al. | |
| 2016/0296577 | A1 | 10/2016 | Piramal et al. | |

FOREIGN PATENT DOCUMENTS

| | | | |
|---|---|---|---|
| CN | 1389561 | A * | 1/2003 |
| CN | 103432029 | A * | 12/2013 |
| CN | 104381568 | | 3/2015 |
| IN | 2007CH01647 | | 9/2009 |

OTHER PUBLICATIONS

Choi J. et al. Roasting Enhances Antioxidant Effect of Bitter Melon Increasing in Flavan-3-ol and Phenolic Acid Contents. Food Science Biotechnology 21(1)19-26, 2012. (Year: 2012).*

Padumanonda T. et al. Determination of Melatonin Content in Traditional Thai Herbal Remedies Used as Sleeping Aids. DARU J Pharmaceutical Sciences 22(6)1-5, 2014. (Year: 2014).*
Udoh, Uduak S., et al., "The Molecular Circadian Clock and Alcohol-Infused Liver Injury," *biomolecules*, 5, pp. 2504-2537 (2015).
Benna, Clara, et al., "Genetic variation of clock genes and cancer risk: a field synopsis and mea-analysis," *Oncotarget*, vol. 8, No. 14, pp. 23978-23995 (2017).
Sjöholm, Louise K., et al., "CLOCK is suggested to associate with Comorbid alcohol use and depressive disorders," *Journal of Circadian Rhythms*, 8:1, 9 pages (2010).
Doi, Ryosuke, et al., "CLOCK regulates Circadian Rhythms of Hepatic Glycogen Synthesis through Transcriptional Activation of Gys2," *The Journal of Biological Chemistry*, vol. 285, No. 29, pp. 22114-22121 (Jul. 16, 2010).
Sundar, Isaac K., et al., "Circadian molecular clock in lung pathophysiology," *Am J Physiol Lung Cel Mol Physiol*, 309: L1056-L1075 (2015).
Hodžić, Alenka, et al., "Genetic Variation in Circadian Rhythm Genes CLOCK and ARNTL as Risk Factor for Male Infertility," *PLOS One*, vol. 8, Issue 3, 5 pages (Mar. 2013).
Vieira, Elaine, et al., "Altered Clock Gene Expression in Obese Visceral Adipose Tissue is Associated with Metabolic Syndrome," *PLOS One*, vol. 9, Issue 11, 11 pages (Nov. 2014).
Lefta, Mellani, et al., "Circadian Rhythms, the Molecular Clock, and Skeletal Muscle," *Curr Top Dev Biol.*, vol. 96, pp. 231-271 (2011).
Lu, Chao, et al., "Role of circadian gene Clock during differentiation of Mouse pluripotent stem cells," *Protein Cell*, vol. 7, No. 11, pp. 820-832 (2016).
Paschos, Georgios K., et al., "Obesity in mice with adipocyte-specific deletion of clock component Arntl," *Nat Med*, vol. 18, No. 12, pp. 1768-1777 (Dec. 2012).
Shimba, Shigeki, et al., "Brain and muscle Arnt-like protein-1 (BMAL1), a component of the molecular clock, regulates adipogenesis," *PNAS*, vol. 102, No. 34, pp. 12071-12076 (Aug. 23, 2005).
Kondratov, Roman V., et al., "Early aging and age-related pathologies in ,ice deficient in BMAL1, the core component of the circadian clock," *Genes & Development*, vol. 20, pp. 1868-1873 (2006).
Nievergelt, Caroline M., et al., "Suggestive evidence for association of the circadian genes PERIOD3 and ARNTL with bipolar disorder," *Am J Med. Genet B Neuropsychiatr Genet*, vol. 141B, No. 3, pp. 234-241 (Apr. 5, 2006).
Mullenders, Jasper, et al., "A Large Scale shRNA Barcode Screen Identifies the Circadian Clock Component ARNTL as Putative Regulator of the P53 Tumor Suppressor Pathway," *PLOS One*, vol. 4, Issue 3, 10 pages (Mar. 2009).
Rudic, R. Daniel, "BMAL1 and CLOCK, Two Essential Components of the Circadian Clock, Are Involved in Glucose Homeostasis," *PLOS Biology*, vol. 2, Issue 11, 7 pages (Nov. 2004).
Kennaway, David John, "Global Loss of Bmal1 Expression Alters Adipose Tissue Hormones, Gene Expression and Glucose Metabolism," *PLOS One*, vol. 8, Issue 6, 11 pages (Jun. 2013).

(Continued)

*Primary Examiner* — Ralph J Gitomer
(74) *Attorney, Agent, or Firm* — Christensen, Fonder, Dardi & Herbert PLLC

(57) ABSTRACT

A method for at least one of adjusting the biological clock, improving sleep quality, and facilitating sleep is provided, wherein the method comprises administering to the subject an effective amount of a *Momordica charantia* extract, wherein the extract is obtained by extracting a fruit of *Momordica charantia* with water.

5 Claims, 2 Drawing Sheets

(56) References Cited

OTHER PUBLICATIONS

Woon, Peng Y., et al., "Aryl hydrocarbon receptor nuclear translocator-like (BMAL1) is associated with susceptibility to hypertension and type 2 diabetes," *PNAS*, vol. 104, No. 36, pp. 14412-14417 (Sep. 4, 2007).
Pillai, Renjitha, et al., "Aryl Hydrocarbon Receptor Nuclear Translocator/Hypoxia-inducible Factor-1β Plays a Critical Role in Maintaining Glucose-Stimulated Anaplerosis and Insulin Release from Pancreatic β-Cells," *The Journal of Biological Chemistry*, vol. 286, No. 2, pp. 1014-1024 (Jan. 14, 2011).
Gu, Zhuqin, et al., "Association of ARNTL and PER1 genes with Parkinson's Disease: a case-control study of Han Chinese," *Scientific Reports*, 5:15891, 10 pages (2015).
Storch, Kai-Florian, et al., "Intrinsic circadian clock of the mammalian Retina: importance for retinal processing of visual information," *Cell*, vol. 130, No. 4, pp. 730-741 (Aug. 24, 2007).
Ratajczak, Christine K., "Impaired Steroidogenesis and Implantation Failure in Bmal1 Mice," *Endocrinology*, vol. 150, No. 4, pp. 1879-1885 (Apr. 2009).
Woon, Peng Y., "Aryl hydrocarbon receptor nuclear translocator-like (BMAL1) is associated with susceptibility to hypertension and type 2 diabetes," *PNAS*, vol. 104, No. 36, pp. 14412-14417 (Sep. 4, 2007).
Anea, Ciprian B., et al., "Vascular disease in mice with a dysfunctional circadian clock," *Circulation*, vol. 119, No. 11, pp. 1510-1517 (Mar. 24, 2009).
Chou, Chu-Fang, et al., "KSRP is critical in governing hepatic lipid metabolism through controlling Per2 expression," *Journal of Lipid Research*, vol. 56, pp. 227-240 (2015).
Englund, Ani, et al., "NPAS2 and PER2 are linked to risk factors of the metabolic syndrome," *Journal of Circadian Rhythms*, vol. 7, No. 5, 9 pages (May 26, 2009).
Sun, Yuan-Yuan, et al., "Period 2 is essential to maintain early endothelial progenitor cell function in vitro and angiogenesis after myocardial infarction in mice," *J. Cell. Mol. Med.*, vol. 18, No. 5, pp. 907-918 (2014).
Kalfalah, Faiza, et al., "Crosstalk of clock gene expression and autophagy in aging," *Aging*, vol. 8, No. 9, pp. 1876-1895 (2016).
Yoo, Yeong-Min, et al., "Decreased Bone Volume and Bone Mineral Density in the Tibial Trabecular Bone is Associated with Per2 Gene by 405 Nm Laser Stimulation," *Int J. Mol Sci.*, vol. 16, No. 11, pp. 27401-27410 (2015).
Wang, Rui-Hong, et al., "Negative reciprocal regulation between Sirt1 and Per2 modulates the circadian clock and aging," *Sci. Rep.*, vol. 6, 15 pages (2016).
Shumay, E., et al., "Repeat variation in the human PER2 gene as a new genetic marker associated with cocaine addiction and brain dopamine D2 Receptor availability," *Transl. Psychiatry*, vol. 2, 9 pages (2012).
Bhatwadekar, Ashay D., "Per2 Mutation Recapitulates the Vascular Phenotype of Diabetes in the Retina and Bone Marrow," *Diabetes*, vol. 62, pp. 273-282 (Jan. 2013).
Lee, Heon-Jeong, et al., "PER2 Variation is Associated with Diurnal Preference in a Korean Young Population," *Behav Genet*, vol. 41, pp. 273-277 (2011).
Zhao, Han, et al., "Prognostic relevance of Period1 (Per1) and Period2 (Per2) expression in human gastric cancer," *Int J Clin Exp Pathol*, vol. 7, No. 2, pp. 619-630 (2014).
Zani, Fabio, et al., "PER2 promotes glucose storage to liver glycogen during feeding and acute fasting by inducing Gys2 PTG and $G_L$ expression," *Molecular Metabolism*, vol. 2, pp. 292-305 (2013).
Grimaldi, Benedetto, et al., "PER2 Controls Lipid Metabolism by Direct Regulation of PPARγy," *Cell Metab.*, vol. 12, No. 5, pp. 509-520 (2010).
Liu, Bin, et al., "Aberrant expression of Per1 , Per2 and Per3 and their prognostic relevance in non-small cell lung cancer," *Int J Clin Exp Pathol*, vol. 7, No. 11, pp. 7863-7871 (2014).
Wang, Zhaoxia, et al., "Effects of Per2 overexpression on growth inhibition and metastasis, and on MTA1, NM23-H1 and the autophagy-associated PI3K/PKB signaling pathway in nude mice xenograft models of Ovarian cancer," *Molecular Medicine Reports*, vol. 13, pp. 4561-4568 (2016).
Magnone, Maria Chiara, et al., "The mammalian circadian clock gene Per2 modulates cell death in response to oxidative stress," *Front Neurol.*, vol. 5, Article 289, 11 pages (Jan. 2015).
Hwang-Verslues, Wendy W., et al., "Loss of corepressor PER2 under hypoxia up-regulates OCT1-mediated EMT gene expression and enhances Tumor malignancy," *PNAS*, vol. 110, No. 30, pp. 12331-12336 (Jul. 23, 2013).
Hsueh-Ling Cheng, "Screening from bitter gourd for active natural substances that can improve insulin resistance," 18 pages (2008).
Chien-Yun Hsiang et al., "Research for bitter gourd protein on the mechanism of blood sugar regulation and its application," 16 pages (2008).
Ching-Jang Huang et al., "Extraction and chemical identification from bitter gourd for PPAR-activated ingredients and its use in the development of an insulin sensitivity regulator and a blood lipid health food," 8 pages (2008).
Sing Pei Tan et al., "An Optimised Aqueous Extract of Phenolic Compounds from Bitter Melon with High Antioxidant Capacity," *Antioxidants*, 3, pp. 814-829 (2014).
Choi, Jine Shang, et al., "Roasting Enhances Antioxidant Effect of Bitter Melon (*Momordica charantia* L.) Increasing in Flavan-3-ol and Phenolic Acid Contents," *Food Sci. Biotechnol*, 21(1), pp. 19-26 (2012).

\* cited by examiner

METHOD FOR REGULATING CIRCADIAN CLOCK, REGULATING DIURNAL PREFERENCE, ADJUSTING A BIOLOGICAL CLOCK, IMPROVING SLEEP QUALITY AND/OR FACILITATING SLEEP BY USING MOMORDICA CHARANTIA EXTRACT

CROSS REFERENCE TO RELATED APPLICATIONS

This application is a continuation-in part of U.S. application Ser. No. 15/629,058, filed on Jun. 21, 2017, which claims priority to U.S. Provisional Application Ser. No. 62/352,767 filed on Jun. 21, 2016, in the United States Patent and Trademark Office, the disclosures of which are incorporated herein in their entirety by reference.

FIELD OF THE INVENTION

The present invention relates to uses of a *Momordica charantia* extract, especially an extract of a roasted fruit of *Momordica charantia*, the uses include treating or preventing diseases related to CLOCK gene, ARNTL gene, and/or PER2 gene, and regulating physiological functions related to the genes. The present invention especially relates to the use of the extract in at least one of adjusting the biological clock, improving sleep quality, and facilitating sleep.

BACKGROUND OF THE INVENTION

Circadian rhythm is a change of a roughly 24-hour cycle in vital activities (e.g., food intake, body activities, sleep, awakening of animals), which is driven by a circadian clock. When the circadian rhythm of human bodies is disturbed, it will lead to changes in the body's biological clock, decrease in sleep quality, irregularity of hormonal secretion, and decrease in the ability to act. Thus, work efficiency will be reduced, probability of accidents will increase, and many diseases (e.g., depressive disorder) may be induced.

Currently, Diazepam and Lorazepam are common drugs used in clinic for regulating circadian rhythm to treat related diseases such as insomnia and depressive disorder. However, patients are prone to addiction after using the aforementioned drugs and may have side effects, such as hypersomnia, nausea, headache, vomiting, gastrointestinal discomfort, memory impairment, rebound insomnia, unconsciousness, ataxia, dyspnea, and/or somnambulism. Therefore, there is necessity and urgency for continuously developing a drug or method for regulating circadian rhythm effectively without causing addictions and side effects.

It was revealed by researches that a human body's circadian rhythm and sleep cycle are regulated by the expressions of genes including CLOCK (circadian locomotor output cycles kaput), ARNTL (aryl hydrocarbon receptor nuclear translocator like), and PER2 (period circadian clock 2). Thus, if the expressions of CLOCK gene, ARNTL gene, and PER2 gene could be increased, the circadian rhythm will be effectively regulated which is beneficial to adjust a biological clock, improve sleep quality and facilitate sleep.

Inventors of the present invention found that *Momordica charantia* extract is effective in regulating the expressions of genes, i.e., CLOCK, ARNTL, and PER2 genes, and thus, can be used for adjusting the biological clock, improving sleep quality, and/or facilitating sleep, as well as can be used for treating or preventing diseases related to the aforementioned genes, and/or regulating physiological functions related to the aforementioned genes. Preferably, the *Momordica charantia* extract is an extract of a roasted fruit of *Momordica charantia*.

SUMMARY OF THE INVENTION

An objective of the present invention is to provide a use of *Momordica charantia* extract in the manufacture of a medicament, wherein the medicament is for increasing the expressions of at least one of CLOCK, ARNTL, and PER2 genes. Preferably, the medicament is used for treating or preventing diseases related to the aforementioned genes, and/or regulating physiological functions related to the aforementioned genes. The disease related to CLOCK gene, ARNTL gene, and/or PER2 gene is at least one of cancer (including gastric cancer, lung cancer, and ovarian cancer), alcohol-induced liver injury, depressive disorder, bipolar disorder, male infertility, aging, Parkinson's disease, vascular disease, metabolic syndrome (including obesity, hypertension, and diabetes mellitus), and cocaine addiction. The physiological function related to CLOCK gene, ARNTL gene, and/or PER2 gene is at least one of glycogen synthesis, lung pathophysiology, maintenance and adaption of skeletal muscles, maintenance and differentiation of pluripotent stem cells, glucose homeostasis, glucose metabolism, insulin release, adipogenesis, retinal function, steroidogenesis, hepatic lipid metabolism, angiogenesis, autophagy in aging, maintenance of bone volume and bone density, circadian clock, diurnal preference, glycogen metabolism, lipid metabolism, endothelial progenitor cell function, and oxidative injury. Preferably, the *Momordica charantia* extract is obtained by extracting a fruit of *Momordica charantia* with water. Preferably, the *Momordica charantia* extract is an extract of a roasted fruit of *Momordica charantia*, and the roasted fruit of *Momordica charantia* is provided by subjecting a fruit of *Momordica charantia* to a roasting treatment at a temperature ranging from about 80 to 180° C. Preferably, the roasting treatment comprises roasting at a stepwise-increased temperature. Preferably, the roasting treatment comprises a first roasting stage at T1 and a second roasting stage at T2 after the first roasting stage, wherein T1<T2, 80° C.≤T1<180° C., and 80° C.<T2≤180° C. More preferably, the roasting treatment comprises a first roasting stage at T1 and a second roasting stage at T2 after the first roasting stage, wherein T1<T2, 80° C.≤T1≤135° C., and 135° C.≤T2≤180° C.

Another objective of the present invention is to provide a use of the aforesaid *Momordica charantia* extract in the manufacture of a food product, wherein the food product can be used for at least one of adjusting the biological clock, improving sleep quality, and facilitating sleep.

Still another objective of the present invention is to provide a method for increasing the expressions of CLOCK gene, ARNTL gene, and/or PER2 gene in a subject in need, comprising administering to the subject an effective amount of a *Momordica charantia* extract. The method is for treating or preventing diseases related to the aforementioned genes, and/or regulating physiological functions related to the aforementioned genes. The method is for adjusting the biological clock, improving sleep quality, and facilitating sleep. Preferably, the *Momordica charantia* extract is obtained by extracting a fruit of *Momordica charantia* with water. Preferably, the *Momordica charantia* extract is an extract of a roasted fruit of *Momordica charantia*, and the roasted fruit of *Momordica charantia* is provided by subjecting a fruit of *Momordica charantia* to a roasting treatment at a temperature ranging from about 80 to 180° C.

Preferably, the roasting treatment comprises roasting at a stepwise-increased temperature. Preferably, the roasting treatment comprises a first roasting stage at T1 and a second roasting stage at T2 after the first roasting stage, wherein T1<T2, 80° C.≤T1<180° C., and 80° C.<T2≤180° C. More preferably, the roasting treatment comprises a first roasting stage at T1 and a second roasting stage at T2 after the first roasting stage, wherein T1<T2, 80° C.≤T1≤135° C., and 135° C.≤T2≤180° C.

Yet another objective of the present invention is to provide a method for at least one of regulating circadian clock, regulating diurnal preference, adjusting a biological clock, improving sleep quality, and facilitating sleep, comprising administering to a subject in need an effective amount of a *Momordica charantia* extract described above.

Yet another objective of the present invention is to provide a method for providing a *Momordica charantia* extract with enhanced effect on increasing the expressions of CLOCK gene, ARNTL gene, and/or PER2 gene, comprising subjecting a fruit of *Momordica charantia* to a roasting treatment prior to extracting the fruit of *Momordica charantia*, wherein the enhanced effect is enhanced in comparison with a corresponding effect of the extract of unroasted *Momordica charantia* fruit on increasing the expressions of CLOCK gene, ARNTL gene, and/or PER2 gene. Preferably, the roasting treatment comprises roasting the fruit of *Momordica charantia* at a temperature ranging from about 80 to 180° C. Preferably, the roasting treatment comprises roasting at a stepwise-increased temperature. Preferably, the roasting treatment comprises a first roasting stage at T1 and a second roasting stage at T2 after the first roasting stage, wherein T1<T2, 80° C.≤T1<180° C., and 80° C.<T2≤180° C. More preferably, the roasting treatment comprises a first roasting stage at T1 and a second roasting stage at T2 after the first roasting stage, wherein T1<T2, 80° C.≤T1≤135° C., and 135° C.≤T2≤180° C.

The detailed technology and some particular embodiments implemented for the present invention are described in the following paragraphs for people skilled in this field to well appreciate the features of the claimed invention.

DESCRIPTION OF THE PREFERRED EMBODIMENTS

Figure 1:
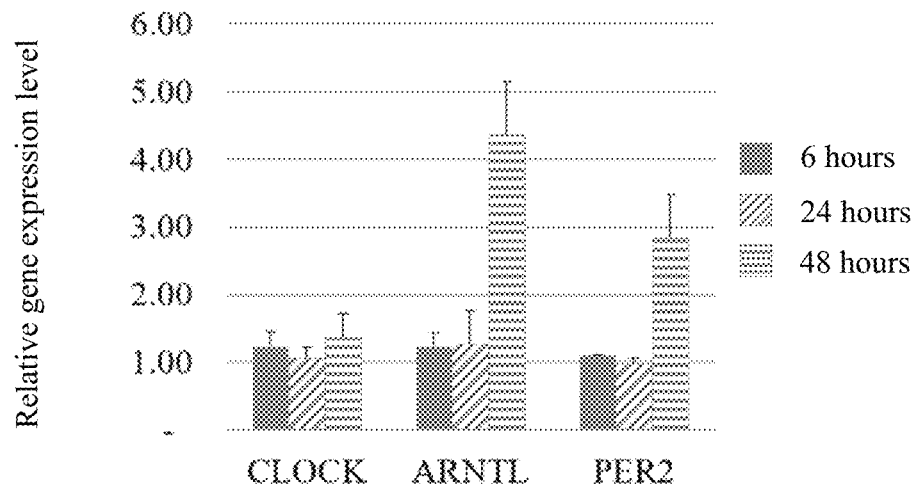
FIG. 1 shows the expression levels of CLOCK, ARNTL, and PER2 genes in the HepG2 cells of different groups (as compared to the expression level of the control group), wherein the cells of "control group" were cultivated in a medium free of any *Momordica charantia* extract for 48 hours, the cells of "6 hours group" and "24 hours group" were cultivated in a medium free of any *Momordica charantia* extract for 24 hours, and then were cultivated in a medium externally added with an unroasted *Momordica charantia* extract for another 6 hours and 24 hours respectively, and the cells of "48 hours group" were cultivated in a medium externally added with an unroasted *Momordica charantia* extract for 48 hours.

The following will describe some of the embodiments of the present invention in detail. However, without departing from the spirit of the present invention, the present invention may be embodied in various embodiments and should not be limited to the embodiments described in the specification or defined in the appended claims.

In addition, unless otherwise indicated herein, the expressions "a," "an," "the," or the like recited in the specification of the present invention (especially in the claims) are intended to include both the singular and plural forms. The term "treat" or "treating" recited in this specification should not be construed as treating a subject until the subject is completely recovered, but should include maintaining the progression or symptoms of the diseases in a substantially static state, increasing the recovery rate of a subject, alleviating the severity of a particular condition of illness, or increasing the life quality of patients. The term "prevent" or "preventing" recited in this specification refers to inhibiting or preventing a particular condition of illness from breaking out, or maintaining good health in a sensitive subject to tolerate diseases. The term "regulate" or "regulating" recited in this specification refers to upregulating (includes inducing, stimulating, and enhancing) or downregulating (includes inhibiting and weakening) the physiological functions in a subject toward a normal state. The term "an effective amount" recited in this specification refers to the amount of the substance that can at least partially alleviate the condition that is being treated in a suspected subject when administered to the subject. The term "subject" recited in this specification refers to a mammalian, including human and non-human animals.

*Momordica charantia* is a plant belonging to the family Cucurbitaceae. In general, *Momordica charantia* originally habitats in the tropics, and is widely planted in South Asia, Southeast Asia, Taiwan, China, and Caribbean islands. In Taiwan, *Momordica charantia* is commonly distributed in Taichung, Changhua, Chiayi, and Kaohsiung.

As described above, inventors of the present invention found that the *Momordica charantia* extract, particular an extract of a roasted fruit of *Momordica charantia*, is effective in regulating the expressions of CLOCK, ARNTL, and PER2 genes. It has been known that CLOCK gene is positively related to the treatment, prevention, or regulation of alcohol-induced liver injury, cancer, depressive disorder, glycogen synthesis, lung pathophysiology, male infertility, obesity, as well as maintenance and adaption of skeletal muscles, maintenance and differentiation of pluripotent stem cells. Therefore, if the expression of CLOCK gene can be increased, the diseases related to CLOCK gene can be treated or prevented, and the physiological functions related to CLOCK gene can be regulated. The correlation between CLOCK gene and the aforementioned diseases and physiological functions can be seen in, for example, "The Molecular Circadian Clock and Alcohol-Induced Liver Injury. *Biomolecules*. 5: 2504-2537 (2015);" "Genetic variation of clock genes and cancer risk: a field synopsis and meta-analysis. *Oncotarget*. Vol. 8, (No. 14), pp: 23978-23995 (2017);" "CLOCK is suggested to associate with comorbid alcohol use and depressive disorders. *Journal of*

*Circadian Rhythms.* 8:1 (2010);" "CLOCK Regulates Circadian Rhythms of Hepatic Glycogen Synthesis through Transcriptional Activation of Gys2. *The journal of biological chemistry*. Vol. 285, No. 29, pp. 22114-22121 (2010);" "Circadian molecular clock in lung pathophysiology. *Am J Physiol Lung Cell Mol Physiol*. 309: L1056-L1075 (2015);" "Genetic Variation in Circadian Rhythm Genes CLOCK and ARNTL as Risk Factor for Male Infertility. *PLoS One.* 8(3):e59220 (2013);" "Altered Clock Gene Expression in Obese Visceral Adipose Tissue Is Associated with Metabolic Syndrome. *PLoS One*. November 3; 9(11):e111678 (2014);" "Circadian Rhythms, the Molecular Clock, and Skeletal Muscle. *Curr Top Dev Biol*. 96: 231-271 (2011);" and "Role of circadian gene Clock during differentiation of mouse pluripotent stem cells. *Protein Cell*. 7(11):820-832 (2016)," which are entirely incorporated hereinto by reference.

It has been known that ARNTL gene is positively related to the treatment, prevention, or regulation of obesity, adipogenesis, aging, bipolar disorder, cancer, glucose homeostasis, glucose metabolism, hypertension, insulin release, male infertility, Parkinson's disease, retinal function, steroidogenesis, type II diabetes mellitus, and vascular disease. Therefore, if the expression of ARNTL gene can be increased, the diseases related to ARNTL gene can be treated or prevented, and the physiological functions related to ARNTL gene can be regulated. The correlation between ARNTL gene and the aforementioned diseases or physiological functions can be seen in, for example, "Obesity in mice with adipocyte-specific deletion of clock component Arntl. *Nat Med*. 18(12): 1768-1777 (2012);" "Brain and muscle Arnt-like protein-1 (BMAL1), a component of the molecular clock, regulates adipogenesis. *Proc Natl Acad Sci USA*. 102(34):12071-6 (2005);" "Early aging and age-related pathologies in mice deficient in BMAL1, the core component of the circadian clock. *Genes Dev.* 20(14):1868-73 (2006);" "Suggestive evidence for association of the circadian genes PERIOD3 and ARNTL with bipolar disorder. *Am J Med Genet B Neuropsychiatr Genet.* 141B(3): 234-241 (2006);" "A Large Scale shRNA Barcode Screen Identifies the Circadian Clock Component ARNTL as Putative Regulator of the p53 Tumor Suppressor Pathway. *PLoS One.* 4(3):e4798 (2009);" "BMAL1 and CLOCK, Two Essential Components of the Circadian Clock, Are Involved in Glucose Homeostasis. *PLoS Biol.* November 2(11):e377 (2004);" "Global Loss of Bmal1 Expression Alters Adipose Tissue Hormones, Gene Expression and Glucose Metabolism. *PLoS One.* June 4; 8(6):e65255 (2013);" "Aryl hydrocarbon receptor nuclear translocator-like (BMAL1) is associated with susceptibility to hypertension and type 2 diabetes. *Proc Natl Acad Sci USA*. 104(36):14412-7 (2007);" "Aryl Hydrocarbon Receptor Nuclear Translocator/Hypoxiainducible Factor-1β Plays a Critical Role in Maintaining Glucose-stimulated Anaplerosis and Insulin Release from Pancreatic β-Cells. *J Biol Chem*. 286(2):1014-24 (2011);" "Genetic variation in circadian rhythm genes CLOCK and ARNTL as risk factor for male infertility. *PLoS One.* 8(3):e59220 (2013);" "Association of ARNTL and PER1 genes with Parkinson's disease: a case-control study of Han Chinese. *Sci Rep.* 5:15891 (2015);" "Intrinsic circadian clock of the mammalian retina: importance for retinal processing of visual information. *Cell*. 130(4):730-41 (2007);" "Impaired steroidogenesis and implantation failure in Bmal1−/− mice. *Endocrinology*. April; 150(4):1879-85 (2009);" "Aryl hydrocarbon receptor nuclear translocator-like (BMAL1) is associated with susceptibility to hypertension and type 2 diabetes. *Proc Natl Acad Sci USA*. September 4; 104(36):14412-7 (2007);" and "Vascular disease in mice with a dysfunctional circadian clock. *Circulation*. 119(11):1510-7 (2009)," which are entirely incorporated hereinto by reference.

It has been known that PER2 gene is positively related to the treatment, prevention, or regulation of hepatic lipid metabolism, metabolic syndrome, angiogenesis, autophagy in aging, bone volume and bone density, aging, circadian clock, cocaine addiction, diabetes mellitus, diurnal preference, endothelial progenitor cell function, gastric cancer, glycogen metabolism, lung cancer, ovarian cancer, and oxidative injury. The correlation between PER2 gene and the aforementioned diseases and physiological functions can be seen in, for example, "KSRP is critical in governing hepatic lipid metabolism through controlling Per2 expression. *J Lipid Res.* 56(2):227-40. (2015);" "NPAS2 and PER2 are linked to risk factors of the metabolic syndrome. *J Circadian Rhythms*. 26; 7:5. (2009);" "Period 2 is essential to maintain early endothelial progenitor cell function in vitro and angiogenesis after myocardial infarction in mice. *J Cell Mol Med.* 18(5):907-18 (2014);" "Crosstalk of clock gene expression and autophagy in aging. *Aging (Albany N.Y.)*. 8(9):1876-1895 (2016);" "Decreased Bone Volume and Bone Mineral Density in the Tibial Trabecular Bone Is Associated with Per2 Gene by 405 nm Laser Stimulation. *Int J Mol Sci.* 16(11):27401-10 (2015);" "Negative reciprocal regulation between Sirt1 and Per2 modulates the circadian clock and aging. *Sci Rep.* 6:28633. (2016);" "Repeat variation in the human PER2 gene as a new genetic marker associated with cocaine addiction and brain dopamine D2 receptor availability. *Transl Psychiatry.* 2:e86. (2012);" "Per2 mutation recapitulates the vascular phenotype of diabetes in the retina and bone marrow. *Diabetes*. 62(1):273-82. (2013);" "PER2 Variation is Associated with Diurnal Preference in a Korean Young Population. *Behav Genet.* 41(2):273-7. (2011);" "Period 2 is essential to maintain early endothelial progenitor cell function in vitro and angiogenesis after myocardial infarction in mice. *J Cell Mol Med.* 18(5):907-18. (2014);" "Prognostic relevance of Period1 (Per1) and Period2 (Per2) expression in human gastric cancer. *Int J Clin Exp Pathol.* 15; 7(2):619-30. (2014);" "PER2 promotes glucose storage to liver glycogen during feeding and acute fasting by inducing Gys2 PTG and G L expression. *Mol Metab.* 2(3):292-305. (2013);" "PER2 controls lipid metabolism by direct regulation of PPARγ. *Cell Metab.* 12(5):509-20. (2010);" "Aberrant expression of Per1, Per2 and Per3 and their prognostic relevance in non-small cell lung cancer. *Int J Clin Exp Pathol.* 7(11):7863-71 (2014);" "Effects of Per2 overexpression on growth inhibition and metastasis, and on MTA1, nm23-H1 and the autophagy-associated PI3K/PKB signaling pathway in nude mice xenograft models of ovarian cancer. *Mol Med Rep.* 13(6):4561-8. (2016);" "The Mammalian circadian clock gene per2 modulates cell death in response to oxidative stress. *Front Neurol.* 5:289. (2015);" and "Loss of corepressor PER2 under hypoxia up-regulates OCT1-mediated EMT gene expression and enhances tumor malignancy. *Proc Natl Acad Sci USA*. 110(30):12331-6 (2013)," which are entirely incorporated hereinto by reference.

Thus, the present invention provides a use of *Momordica charantia* extract in the manufacture of a medicament for increasing the expressions of at least one of CLOCK, ARNTL, and PER2 genes. Preferably, the *Momordica charantia* extract is obtained by extracting a fruit of *Momordica charantia* with water. Preferably, the medicament is used for treating or preventing diseases related to the aforementioned genes, and/or regulating physiological functions related to the aforementioned genes.

The disease related to CLOCK gene, ARNTL gene, and/or PER2 gene is at least one of cancer (including gastric cancer, lung cancer, and ovarian cancer), alcohol-induced liver injury, depressive disorder, bipolar disorder, male infertility, aging, Parkinson's disease, vascular disease, metabolic syndrome (including obesity, hypertension, and diabetes mellitus), and cocaine addiction.

The physiological function related to CLOCK gene, ARNTL gene, and/or PER2 gene is at least one of glycogen synthesis, lung pathophysiology, maintenance and adaption of skeletal muscles, maintenance and differentiation of pluripotent stem cells, glucose homeostasis, glucose metabolism, insulin release, adipogenesis, retinal function, steroidogenesis, hepatic lipid metabolism, angiogenesis, autophagy in aging, maintenance of bone volume and bone density, circadian clock, diurnal preference, glycogen metabolism, lipid metabolism, endothelial progenitor cell function, and oxidative injury.

Furthermore, inventors of the present invention found that in the uses according to the present invention, if an extract of a roasted fruit of *Momordica charantia* (i.e., a fruit of *Momordica charantia* is subjected to a roasting treatment prior to being extracted) is used as the *Momordica charantia* extract, the desired effects on increasing the expressions of CLOCK gene, ARNTL gene, and/or PER2 gene can be further enhanced. Thus, an extract of a roasted fruit of *Momordica charantia* is preferred to be adopted in the above uses.

Therefore, the present invention also provides a method for providing a *Momordica charantia* extract with enhanced effects. The method comprises subjecting a fruit of *Momordica charantia* to a roasting treatment prior to extracting the fruit of *Momordica charantia*. Preferably, the roasting treatment is conducted at a high temperature. For example, the roasting treatment is conducted at a temperature ranging from about 80 to 180° C. More preferably, the roasting treatment is conducted at a stepwise-increased temperature. For example, the roasting treatment comprises at least two stages, i.e., a first roasting stage at T1 and a second roasting stage at T2 after the first roasting stage, wherein T1<T2. Preferably, T1<T2, 80° C.≤T1<180° C., and 80° C.<T2≤180° C.; and more preferably, T1<T2, 80° C.≤T1≤135° C., and 135° C.≤T2≤180° C.

In the method for providing a *Momordica charantia* extract with enhanced effects according to the present invention, the roasting time could be adjusted optionally, as long as the water content of *Momordica charantia* could be reduced. In some embodiments of the present invention, a roasting treatment comprising two stages with a stepwise-increased temperature was adopted, wherein the fruit of *Momordica charantia* was subjected to a first roasting stage at an environment ranging from 90 to 120° C. for 2 to 24 hours, and then to a second roasting stage at an environment ranging from 150 to 180° C. for 20 to 100 minutes.

In the method and use according to the present invention, the *Momordica charantia* (e.g., a roasted fruit of *Momordica charantia*) could be extracted by any suitable method to provide a *Momordica charantia* extract needed by the present invention. For example, the *Momordica charantia* (e.g., a roasted fruit of *Momordica charantia*) could be directly extracted with water, followed by a solid-liquid separating approach (e.g., filtration) to obtain a liquid extract. Optionally, the liquid extract could be further subjected to the other operations such as concentration and/or drying to obtain a *Momordica charantia* extract in a form of liquid or solid.

Depending on the desired purpose(s), the medicament provided according to the present invention could be provided in any suitable form without particular limitations. For example, the medicament could be administered to a subject in need by an oral or parenteral (such as transdermal administration, nasal administration, subcutaneous injection, intravenous injection, muscular injection, peritoneal injection, subcutaneous implantation, or interstitial implantation) route, but the administration is not limited thereby. Depending on the form and purpose(s), a suitable carrier could be chosen and used to provide the medicament, as long as the carriers do not adversely affect the desired effects of the *Momordica charantia* extract of the present invention. Examples of the carrier could be, but are not limited to excipients, diluents, auxiliaries, stabilizers, absorbent retarders, disintegrating agents, hydrotropic agents, emulsifiers, antioxidants, adhesives, binders, tackifiers, dispersants, suspending agents, lubricants, hygroscopic agents, etc.

As a form suitable for oral administration, examples of the carrier include, but are not limited to, water, saline, dextrose, glycerol, ethanol or its analogs, cellulose, starch, sugar bentonite, and combinations thereof. The medicament could be provided in any suitable form for oral administration, such as in a solid form of a tablet, a pill, a capsule, granules, a pulvis, etc., or in a liquid form of an oral liquid, a syrup, a spirit, an elixir, a tincture, etc., but the form is not limited thereby.

As for the form of injections or drips suitable for subcutaneous, intravenous, muscular, or peritoneal administration, the medicament provided according to the present invention could comprise one or more ingredient(s), such as an isotonic solution, a salt-buffered saline (e.g., phosphate-buffered saline or citrate-buffered saline), a hydrotropic agent, an emulsifier, 5% sugar solution, and other carriers to provide the medicament as an intravenous infusion, an emulsified intravenous infusion, a powder for injection, a suspension for injection, or a powder suspension for injection, etc. Alternatively, the medicament could be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need. In addition, as for the external dosage form for nasal or transdermal administration, the medicament could be provided in the form of, for example, a liniment (such as an emulsion, a cream, a gel, a dispersing paste, an ointment), a spray, a patch, or a solution (such as a cleaning liquid, a suspension), but is not limited thereby.

In the medicament provided according to the use of the present invention, the concentration of *Momordica charantia* extract in the medicament could be adjusted depending on practical requirements.

Optionally, the medicament provided according to the present invention could further comprise a suitable amount of additives, such as flavoring agent, a toner, or a coloring agent for enhancing the palatability and the visual perception of the medicament, and/or a buffer, a conservative, a preservative, an antibacterial agent, or an antifungal agent for improving the stability and storability of the medicament. In addition, the medicament could optionally further comprise one or more other active ingredient(s), or be used in combination with a medicament comprising one or more other active ingredient(s), to further enhance the effect of the medicament, or to increase the application flexibility and adaptability of the preparation thus provided, as long as the other active ingredients do not adversely affect the desired effects of *Momordica charantia* extract.

Depending on the needs, age, body weight, and health conditions of the subject, the medicament provided according to the present invention could be dosed with various administration frequencies, such as once a day, multiple times a day, or once every few days, etc.

As described above, inventors of the present invention found that the *Momordica charantia* extract, particular an extract of a roasted fruit of *Momordica charantia*, is effective in regulating the expressions of CLOCK, ARNTL, and PER2 genes, and thus, can be used for adjusting the physiological clock, improving sleep quality, and facilitating sleep. Therefore, the present invention also provides a use of the aforesaid *Momordica charantia* extract in the manufacture of a food product, wherein the food product is used for at least one of adjusting the physiological clock, improving sleep quality, and facilitating sleep.

The food product provided according to the present invention could be a health food, a nutritional supplement food, or a special nutritional food. The food product could be provided as dairy products, meat products, breadstuff, pasta, cookies, troche, capsule, fruit juices, teas, sport beverages, nutritional beverages, etc., but is not limited thereby. Preferably, the food product provided according to the present invention is a health food.

Depending on the age, body weight and health conditions of the subject, the health food, nutritional supplement food and special nutritional food provided according to the present invention could be taken in various frequencies, such as once a day, multiple times a day or once every few days, etc. The concentration of *Momordica charantia* extract in the health food, nutritional supplement food and special nutritional food provided according to the present invention could be adjusted, preferably to the amount that should be taken daily, depending on the specific population.

The recommended daily dosage, use standards and use conditions for a specific population (e.g., insomnia, circadian desynchronization), or the recommendations for a use in combination with another food product or medicament could be indicated on the exterior package of the health food, nutritional supplement food and/or special nutritional food provided by the present invention. Thus, it is suitable for the user to take the health food, nutritional supplement food and/or special nutritional food by him- or herself safely and securely without the instruction of a doctor, pharmacist, or related executive. In the food product provided according to the present invention, the administration type, suitable administration amount and uses of *Momordica charantia* extract are all in line with the above description.

The present invention also provides a method for increasing the expressions of CLOCK gene, ARNTL gene, and/or PER2 gene in a subject in need, comprising administering to the subject an effective amount of a *Momordica charantia* extract, wherein "a subject in need" refers to a subject whose CLOCK gene, ARNTL gene, and/or PER2 gene is deleted, mutated, or low-expressed, or a subject suffering from a disease related to CLOCK gene, ARNTL gene, and/or PER2 gene. As described above, the present invention also provides a method for at least one of regulating circadian clock, regulating diurnal preference, adjusting a biological clock, improving sleep quality, and facilitating sleep, comprising administering to a subject in need an effective amount of a *Momordica charantia* extract, wherein "a subject in need" refers to a subject having circadian clock disturbances, biological clock disturbances, and/or sleep disturbances. In the aforesaid method, the administration type, administration route, administration form, administration frequency and uses of *Momordica charantia* extract are all in line with the above description.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Preparation Examples

A. Preparation of Unroasted *Momordica charantia* Extract

A fruit (including seeds) of *Momordica charantia* was washed, and then soaked in water (fruit of *Momordica charantia*: water=1:5 in weight) and stewed at 80° C. for 30 minutes to provide a crude liquid extract. Then, the crude liquid extract was filtrated with a 200 mesh filter to provide a liquid extract. Finally, the liquid extract was concentrated four folds to provide an extract (hereinafter referred to as "unroasted *Momordica charantia* extract").

B. Preparation of Roasted *Momordica charantia* Extract

A fruit (including seeds) of *Momordica charantia* was washed and divided into five groups. Those five groups were respectively roasted with the following conditions of Table 1 (instrument: OV-80 oven, purchased from Firstek company):

TABLE 1

| Groups | Roasting conditions |
| --- | --- |
| Group 1 | Roasted at 120° C. for 2 hours, and then roasted at 150° C. for 80 minutes |
| Group 2 | Roasted at 120° C. for 2 hours, and then roasted at 150° C. for 100 minutes |
| Group 3 | Roasted at 120° C. for 2 hours, and then roasted at 180° C. for 40 minutes |
| Group 4 | Roasted at 120° C. for 2 hours, and then roasted at 150° C. for 60 minutes |
| Group 5 | Roasted at 90° C. for 1 day, and then roasted at 180° C. for 20 minutes |

Thereafter, the roasted fruit of *Momordica charantia* of above each group was subjected to the operating procedures (including extraction, filtration, and concentration) as [Preparation Example A] to provide an extract (hereinafter referred to as "roasted *Momordica charantia* extract").

C. Treatment of Cells

HepG2 cells (provided by American Type Culture Collection (ATCC); number: ATCC® HB-8065) were cultivated in a Dulbecco's modified Eagle's medium (DMEM; purchased from Gibco company) containing 10% bovine serum albumin (purchased from Gibco company) for 24 hours. The cells thus provided were used in the following experiments.

Example 1: Effects of *Momordica charantia* Extract on the Expression Levels of CLOCK, ARNTL, and PER2 Genes (1-1) Effects of Unroasted *Momordica charantia* Extract
HepG2 cells obtained from [Preparation Example C] were divided into four groups and were treated as follows under 5% $CO_2$ at 37° C.:
(A) "Control group": cells were cultivated in a DMEM medium containing 10% bovine serum albumin (i.e., a medium free of any *Momordica charantia* extract) for 48 hours.

(B) "6 hours group": cells were cultivated in a medium free of any *Momordica charantia* extract for 24 hours, and then were cultivated in a medium externally added with the unroasted *Momordica charantia* extract provided by [Preparation Example A] (to the final concentration of 2 mg/ml) for another 6 hours.

(C) "24 hours group": cells were cultivated in a medium free of any *Momordica charantia* extract for 24 hours, and then were cultivated in a medium externally added with the unroasted *Momordica charantia* extract provided by [Preparation Example A] (to the final concentration of 2 mg/ml) for another 24 hours.

(D) "48 hours group": cells were cultivated in a DMEM medium containing 10% bovine serum albumin for 48 hours, but the unroasted *Momordica charantia* extract provided by [Preparation Example A] was externally added to the medium (to the final concentration of 2 mg/ml) before conducting the cultivation.

Thereafter, cells of the above groups were harvested and subjected to RNA extraction with an RNA Lysis buffer (purchased from Geneaid company). The RNA thus obtained was then transcribed into cDNA by using a SuperScript™ Reverse Transcriptase kit (purchased from Invitrogen company). Thereafter, the cDNA was subjected to a real-time quantitative polymerase chain reaction (Q-PCR) by using a ABI StepOnePlus™ system (purchased from Applied Biosystems) to determine the expression levels of CLOCK, PER2, ARNTL, and RPLP0 genes in the cells of each group. Then, the expression level of each gene was normalized by using the expression level of RPLP0 gene as a basis. Lastly, the gene expression level of each group was normalized by using that of the control group as a basis. The results are shown in FIG. 1.

As shown in FIG. 1, as compared to the control group (whose gene expression level was served as 1-fold), the expression level of CLOCK gene in the cells of the 48 hours group is 1.35-fold that of the control group, the expression level of ARNTL gene in the cells of the 48 hours group is 4.36-fold that of the control group, and the expression level of PER2 gene in the cells of the 48 hours group is 2.83-fold that of the control group. These results indicate that the *Momordica charantia* extract can significantly increase the expressions of CLOCK, ARNTL, PER2 genes of hepatic cells, and thus, can be used for regulating the human body's physiological clock and/or circadian rhythm.

(1-2) Effects of Roasted *Momordica charantia* Extract

HepG2 cells obtained from [Preparation Example C] were divided into six groups and were treated as follows under 5% $CO_2$ at 37° C.:

(A) "Unroasted group": cells were further divided into three subgroups and separately cultivated in a DMEM medium containing 10% bovine serum albumin for 24 hours, and then were separately cultivated in a DMEM medium externally with the unroasted *Momordica charantia* extract provided by [Preparation Example A](to the final concentration of 2 mg/ml) for another 6 hours, 24 hours, and 48 hours, respectively.

(B) "Roasted 1 group": cells were treated as the "unroasted group", but the unroasted *Momordica charantia* extract provided by [Preparation Example A] was replaced with roasted *Momordica charantia* extract of Group 1 provided by [Preparation Example B].

(C) "Roasted 2 group": cells were treated as the "unroasted group", but the unroasted *Momordica charantia* extract provided by [Preparation Example A] was replaced with roasted *Momordica charantia* extract of Group 2 provided by [Preparation Example B].

(D) "Roasted 3 group": cells were treated as the "unroasted group", but the unroasted *Momordica charantia* extract provided by [Preparation Example A] was replaced with roasted *Momordica charantia* extract of the Group 3 provided by [Preparation Example B].

(E) "Roasted 4 group": cells were treated as the "unroasted group", but the unroasted *Momordica charantia* extract provided by [Preparation Example A] was replaced with roasted *Momordica charantia* extract of Group 4 provided by [Preparation Example B].

(F) "Roasted 5 group": cells were treated as the "unroasted group", but the unroasted *Momordica charantia* extract provided by [Preparation Example A] was replaced with roasted *Momordica charantia* extract of Group 5 provided by [Preparation Example B].

Cells of the above groups were harvested and subjected to RNA extraction, cDNA preparation, and Q-PCR in the order as described in (1-1). Then, the expression levels of CLOCK, PER2, ARNTL genes in the cells of each group were determined. The results are shown in FIGS. 2 to 4, which also had been normalized by using the gene expression level of the control group (i.e., cells were not treated with *Momordica charantia* extract) as a basis.

Figure 2:
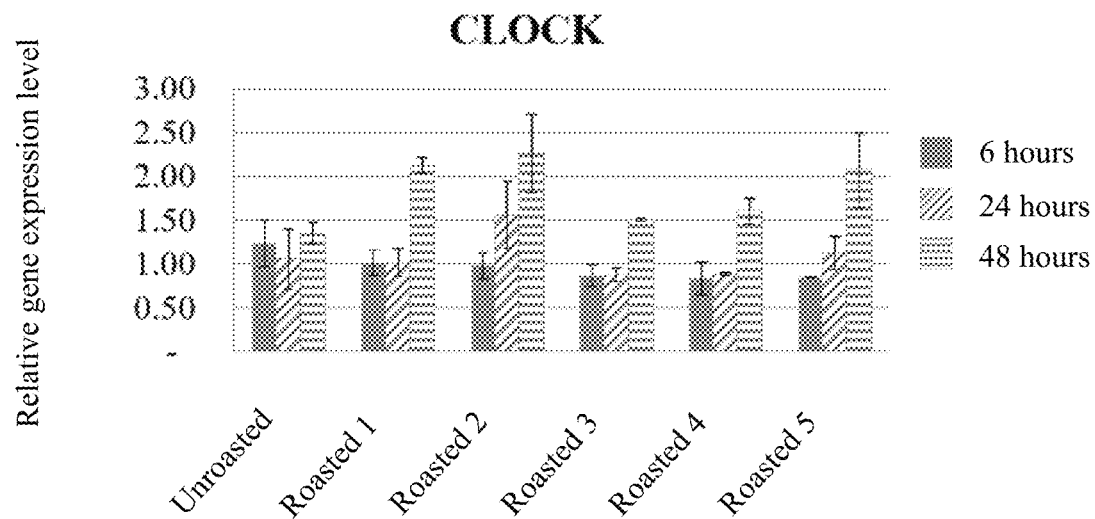
FIG. 2 shows the relative expression level of CLOCK gene in HepG2 cells of different groups (as compared to the expression level of the control group), wherein the cells of the "unroasted groups" were cultivated in the presence of an unroasted *Momordica charantia* extract while the cells of the "roasted 1 groups" to "roasted 5 groups" were cultivated in the presence of a roasted *Momordica charantia* extract.
Figure 3:
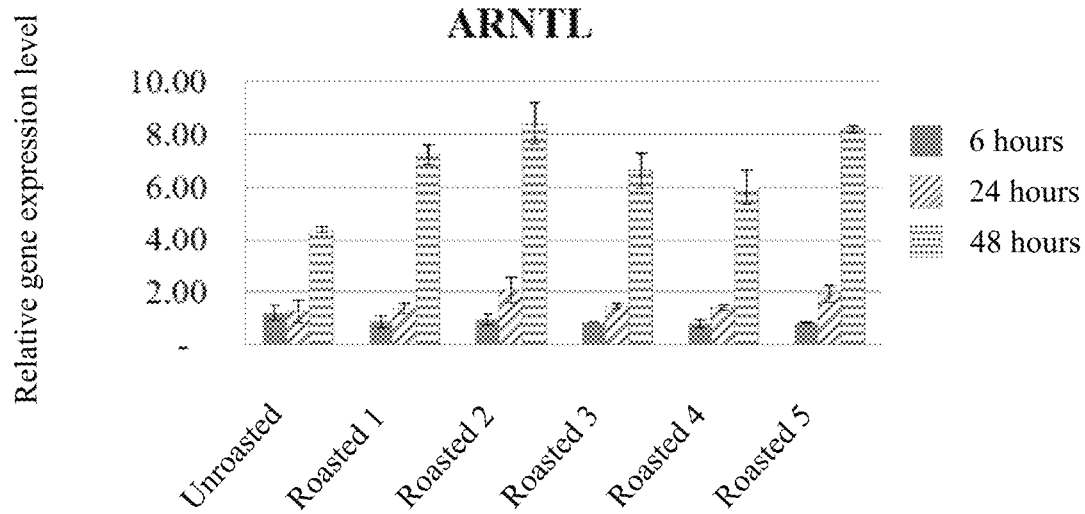
FIG. 3 shows the expression level of ARNTL gene of HepG2 cells in the "unroasted groups" and the "roasted 1 groups" to "roasted 5 groups" described above (as compared to the expression level of the control group).
Figure 4:
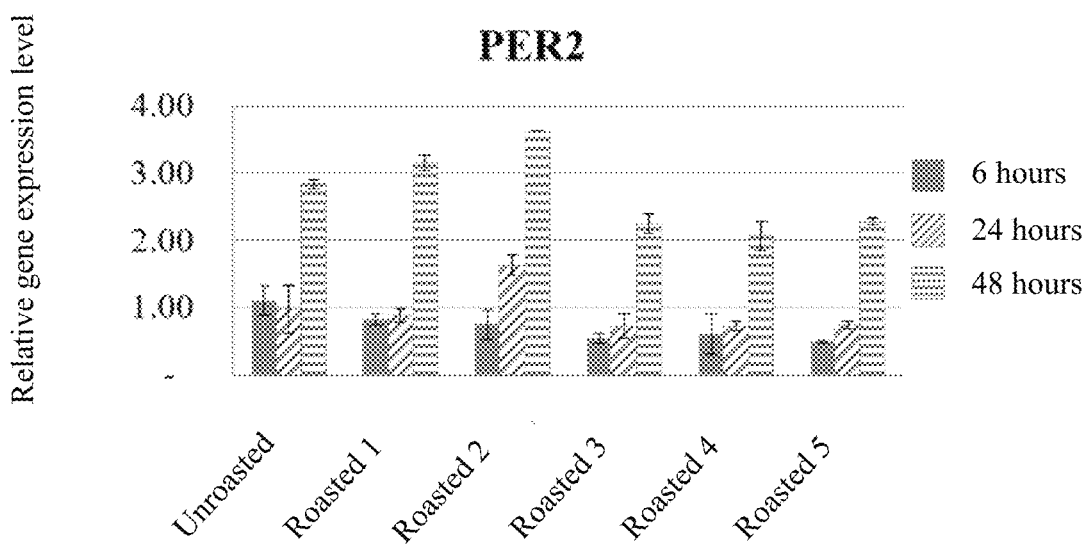
FIG. 4 shows the expression level of PER2 gene of HepG2 cells in the "unroasted groups" and the "roasted 1 groups" to "roasted 5 groups" described above (as compared to the expression level of the control group).

As shown in FIGS. 2 to 4, both the unroasted and roasted *Momordica charantia* extract can exert the best effects of regulating CLOCK, ARNTL, PER2 genes on hepatic cells by a 48 hour-treatment.

Besides, the changing trends of the expression levels of CLOCK, ARNTL, PER2 genes in *Momordica charantia* would vary along with the roasting condition of *Momordica charantia*. As shown in FIG. 2, as compared to the unroasted group, the expression level of CLOCK gene in the cells of the roasted 1 groups to roasted 5 groups all significantly increased. For example, according to the results of the 48 hour-treatment, the expression level of CLOCK gene in the cells of the unroasted group is 1.35-fold that of the control group, and the expression levels of CLOCK gene in the cells of the roasted 1 group to roasted 5 group are respectively 2.12-, 2.26-, 1.50-, 1.60-, and 2.07-fold that of the control group.

As shown in FIG. 3, according to the results of the 48 hour-treatment, the expression level of ARNTL gene in the cells of the unroasted group is 4.36-fold that of the control group, and the expression levels of ARNTL gene in the cells of the roasted 1 group to roasted 5 group are respectively 7.24-, 8.41-, 6.61-, 6.01-, and 8.19-fold that of the control group.

As shown in FIG. 4, according to the results of the 48 hours-treatment, the expression level of PER2 gene in the cells of the unroasted group is 2.83-fold that of the control group. The expression levels of PER2 gene in the cells of the roasted 1 group to roasted 5 group are respectively 3.14-, 3.62-, 2.24-, 2.06-, and 2.27-fold that of the control group.

The above results indicate that, as compared to the unroasted *Momordica charantia* extract (e.g., an extract of an unroasted fruit of *Momordica charantia*), the roasted *Momordica charantia* extract (e.g., an extract of a roasted fruit of *Momordica charantia*) has much excellent effect on increasing the expressions of CLOCK, ARNTL, and PER2 genes of hepatic cells, and thus, can further be used for treating or preventing diseases related to CLOCK, ARNTL, and PER2 genes, and/or regulating physiological functions related to the aforementioned genes, especially can be used for adjusting the physiological clock, improving sleep quality, and/or facilitating sleep.

BRIEF DESCRIPTION OF REFERENCE NUMERALS

Not applicable.

What is claimed is:

1. A method for at least one of regulating circadian clock, regulating diurnal preference, adjusting a biological clock, improving sleep quality, and facilitating sleep in a subject in need, comprising administering to the subject an effective amount of a *Momordica charantia* extract, wherein the extract is obtained by extracting a fruit of *Momordica charantia* with water, and the fruit is a roasted fruit of *Momordica charantia*.

2. The method as claimed in claim 1, wherein the roasted fruit of *Momordica charantia* is provided by subjecting a fruit of *Momordica charantia* to a roasting treatment at a temperature ranging from about 80 to 180° C.

3. The method as claimed in claim 1, wherein the roasted fruit of *Momordica charantia* is provided by subjecting a fruit of *Momordica charantia* to a roasting treatment comprising roasting at a stepwise-increased temperature.

4. The method as claimed in claim 3, wherein the roasting treatment comprises a first roasting stage at T1 and a second roasting stage at T2 after the first roasting stage, wherein T1<T2, 80° C.≤T1<180° C., and 80° C.<T2≤180° C.

5. The method as claimed in claim 4, wherein 80° C.≤T1≤135° C., and 135° C.≤T2≤180° C.

* * * * *